(12) United States Patent
Berube et al.

(10) Patent No.: US 7,684,030 B2
(45) Date of Patent: Mar. 23, 2010

(54) ENCLOSURE FOR A LINEAR INSPECTION SYSTEM

(75) Inventors: Jean Berube, Saint-Nicolas (CA); Marc Voyer, Quebec (CA); Nancy Ferland, Beaupre (CA)

(73) Assignee: VAB Solutions Inc., Lévis, Québec (CA)

( * ) Notice: Subject to any disclaimer, the term of this patent is extended or adjusted under 35 U.S.C. 154(b) by 321 days.

(21) Appl. No.: 11/744,804

(22) Filed: May 4, 2007

(65) Prior Publication Data

US 2008/0273198 A1    Nov. 6, 2008

(51) Int. Cl.
*G01N 21/00*    (2006.01)
(52) U.S. Cl. .................................................... 356/237.1
(58) Field of Classification Search ... 356/237.1–237.5, 356/601–623, 625–635; 250/559.19, 559.24, 250/559.21, 559.25, 559.26
See application file for complete search history.

(56) References Cited

U.S. PATENT DOCUMENTS

| | | | | |
|---|---|---|---|---|
| 3,774,040 A | * | 11/1973 | Stephanos | 250/559.21 |
| 4,301,373 A | | 11/1981 | Sjödin | |
| 4,350,442 A | * | 9/1982 | Arild et al. | 356/51 |
| 4,774,416 A | * | 9/1988 | Askary et al. | 250/492.2 |
| 4,827,142 A | | 5/1989 | Hatje | |
| 4,880,991 A | * | 11/1989 | Boehnlein et al. | 250/559.24 |
| 4,937,445 A | | 6/1990 | Leong et al. | |
| 5,015,867 A | * | 5/1991 | Siegel et al. | 250/559.24 |
| 5,028,798 A | * | 7/1991 | Biswas et al. | 250/559.21 |
| 5,252,836 A | | 10/1993 | Matthews et al. | |
| 5,274,244 A | | 12/1993 | Johansson et al. | |
| 5,568,263 A | * | 10/1996 | Hanna | 356/638 |
| 5,644,392 A | | 7/1997 | Soest et al. | |
| 5,703,960 A | | 12/1997 | Soest | |
| 5,949,086 A | | 9/1999 | Reponen et al. | |
| 6,100,986 A | | 8/2000 | Rydningen | |
| 6,407,818 B1 | * | 6/2002 | Whitehouse | 356/627 |
| 6,466,305 B1 | | 10/2002 | McBain | |
| 6,618,155 B2 | | 9/2003 | Metcalfe et al. | |
| 6,757,058 B1 | | 6/2004 | Carman et al. | |
| 7,200,458 B2 | | 4/2007 | Carman et al. | |
| 2002/0024677 A1 | | 2/2002 | Metcalfe et al. | |
| 2002/0025061 A1 | | 2/2002 | Metcalfe et al. | |
| 2002/0060795 A1 | | 5/2002 | Metcalfe et al. | |
| 2003/0011789 A1 | | 1/2003 | Shirley | |
| 2004/0246473 A1 | | 12/2004 | Hermary et al. | |
| 2005/0031158 A1 | | 2/2005 | Biernacki et al. | |
| 2005/0161118 A1 | | 7/2005 | Carman et al. | |
| 2006/0109485 A1 | * | 5/2006 | Laemmel | 356/635 |

* cited by examiner

*Primary Examiner*—Hoa Q Pham
(74) *Attorney, Agent, or Firm*—Bereskin & Parr LLP/S.E.N.C.R.L., s.r.l.

(57) ABSTRACT

An apparatus for an enclosure of a linear inspection system for the inspection of products that uses at least one camera and at least one laser. The enclosure is placed in a production line environment as to allow the passage of the products to pass through an aperture of the enclosure. More specifically, the enclosure allows to shelter cameras and lasers that are oriented towards an inspection zone through a translucent surface of the enclosure. Furthermore, in another aspect of the invention, the cameras and lasers are fixed to mounting stations in the enclosure. The mounting stations are positioned as to orient the cameras and lasers towards an inspection zone through the translucent surface of the enclosure.

9 Claims, 5 Drawing Sheets

ENCLOSURE FOR A LINEAR INSPECTION SYSTEM

FIELD OF THE INVENTION

The present invention generally relates to the field of industrial measuring equipment. More specifically, the invention relates to an enclosure for a linear inspection system.

BACKGROUND OF THE INVENTION

For many centuries, wood has been a material that has been primarily used in the areas of construction and carpentry. Although not as prevalent as in the past, lumber is still today considered as a very important and useful material for construction, carpentry, cabinet making, etc. Lumber is a natural product that comes from trees and as many natural products, every piece of lumber is different and may have flaws, such as knots, rot, bark, etc. that may or may not be important depending on intended use. For example, the presence of knots in a piece of lumber might be immaterial in carpentry, but undesirable for other types of use, such as for cabinet making.

In order to classify lumber according to intended use or to specific requirements from clients, the lumber industry inspects its lumbers using linear inspection systems. Linear inspection systems use different technology, such as a combination of cameras and lasers, to classify lumber. Typically, the linear inspection system is made of four stations of cameras and lasers placed on top, bottom, right and left of the lumber production line so as to inspect each side of a piece of lumber flowing through the production line. These devices operate in a very demanding environment, filled with dust, debris falling from lumber and the occasional debris flying at high speed. Hence, these delicate electronic instrumentations need to be protected accordingly. Unfortunately, existing linear inspection systems do not always effectively protect the cameras and laser stations. Moreover, the bottom station is often subject to debris accumulation.

There is therefore a need for an improved linear inspection system.

SUMMARY OF THE INVENTION

It is an object of the present invention to provide an enclosure for a linear inspection system that overcomes or mitigates one or more disadvantages of known linear inspection systems, or at least provides a useful alternative.

The invention provides the advantages of efficiently protecting electronic equipment such as cameras and lasers used in linear inspection systems from their harsh operating environment.

The invention further provides the advantage of directing at least some of the debris away from the cameras and lasers.

In accordance with an embodiment of the present invention, there is provided an enclosure to shield the cameras and lasers from dust and debris. The enclosure has an aperture that defines an inspection zone, to allow products to pass through, in a production line environment. In the enclosure, at least one camera and at least one laser are oriented towards the inspection zone through a translucent surface of the enclosure.

In accordance with another embodiment of the present invention, there is provided an enclosure to shield the cameras and lasers from dust and debris. The enclosure has an aperture that defines an inspection zone, to allow products to pass through, in a production line environment. In the enclosure, mounting stations can be placed as to orient a plurality of cameras and lasers towards the inspection zone through a translucent surface of the enclosure. Moreover, the mounting stations are oriented at an angle in a normal plane to a longitudinal axis of the aperture.

BRIEF DESCRIPTION OF DRAWINGS

These and other features of the present invention will become more apparent from the following description in which reference is made to the appended drawings wherein.

DETAILED DESCRIPTION OF THE INVENTION

The present solution relates to an enclosure for a linear inspection system. More precisely, the linear inspection system allows inspecting products. The inspection is required to track given characteristics such as defaults in a product. Thanks to the inspection of such characteristics the classification of the products can be made efficiently.

The enclosure contains cameras and lasers used to inspect moving through products such as lumber. In the case of a lumber production line environment, the presence of dust and wood debris of lumber is common. In such environment, exposed devices such as cameras and lasers can easily be damaged or be obstructed with debris. Hence the need to adequately protect cameras and lasers.

As the inspection process requires precise readings, the calibration of the cameras and laser alignment is done with caution and detail. Consequently, once calibrated, the camera and laser alignment must not be altered by projected debris found in a lumber production line environment. Hence the need for enclosed cameras and lasers is not only for shielding the cameras and lasers from dust and debris but also to prevent the cameras and lasers from losing alignment.

Figure 1:
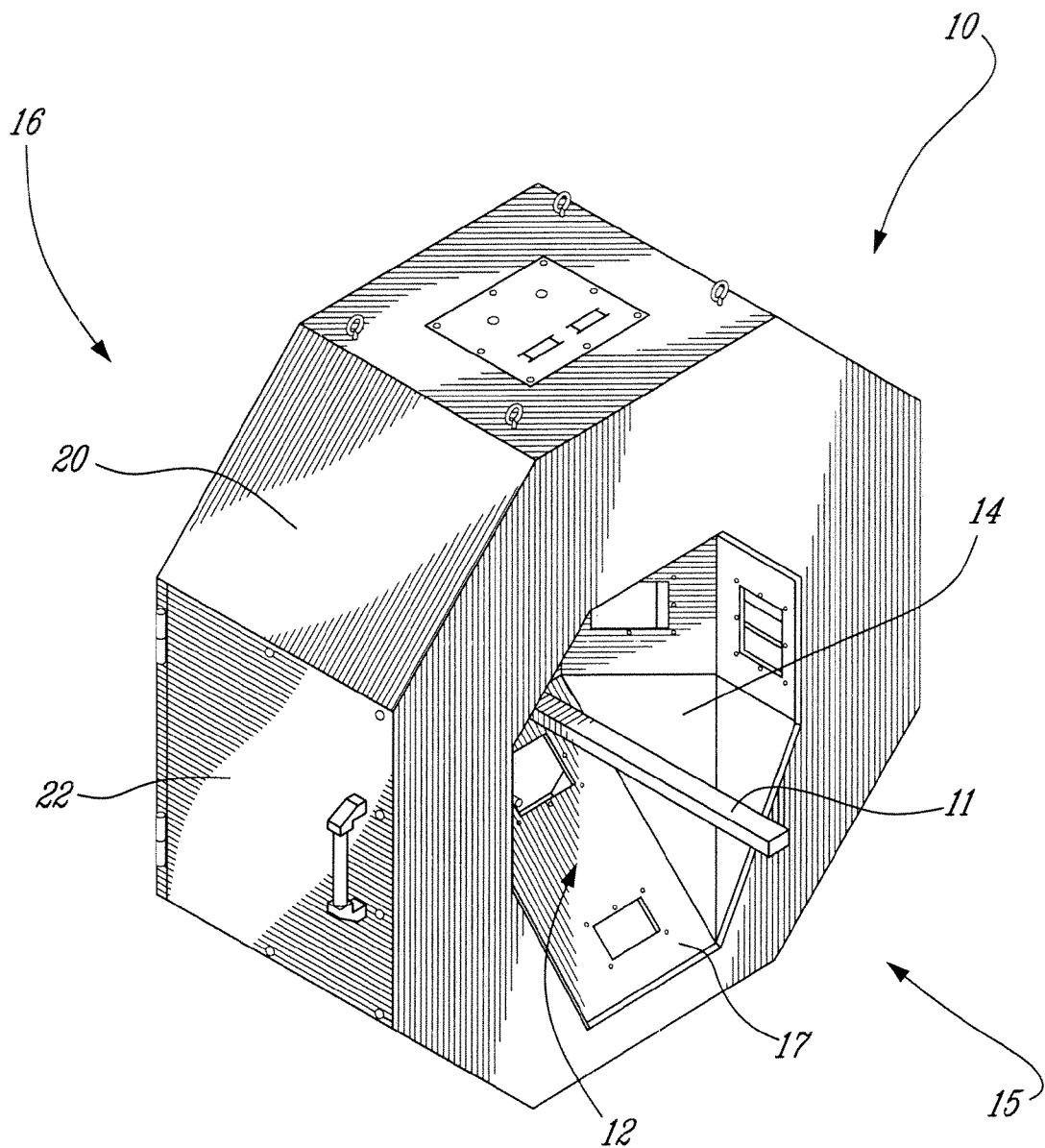
FIG. 1 is a perspective view of an enclosure for a linear inspection system in accordance with an embodiment of the present invention.

Presented in FIG. 1 is a perspective view of an enclosure 10 for a linear inspection system in accordance with an embodiment of the present invention. The enclosure can be made of sheet metal, of a polymer material, or of any shock resistant material that is dust resistant. The enclosure is designed to allow a product 11 to pass through for inspection. The product 11 can be any object that might require to be inspected for flaws or classification on a production line. Such products that require inspection can span from pieces of lumber to metal pipes or even polymer products and more.

The enclosure 10 comprises a central portion 14 that defines an aperture 12, as best seen in FIG. 1. The aperture 12 is large enough to allow a given product 11 to pass through for inspection. The aperture 12 can have any shape, it can be elliptic, polygonal or a combination of both. Consequently, the central portion 14 that defines the aperture 12 can have curved surfaces, flat surfaces or a combination of both.

According to an embodiment of this invention, an output side 15 of the central portion 14 has an irregular octagonal funnel-shaped aperture 12 that decreases towards an inside of the central portion 14 into a square aperture 12. A receiving side 16 of the central portion 14, although not symmetrical to the output side 15, has a regular octagonal funnel-shaped aperture 12 further decreasing towards the inside of the central portion 14 into a square aperture 12.

Figure 2:
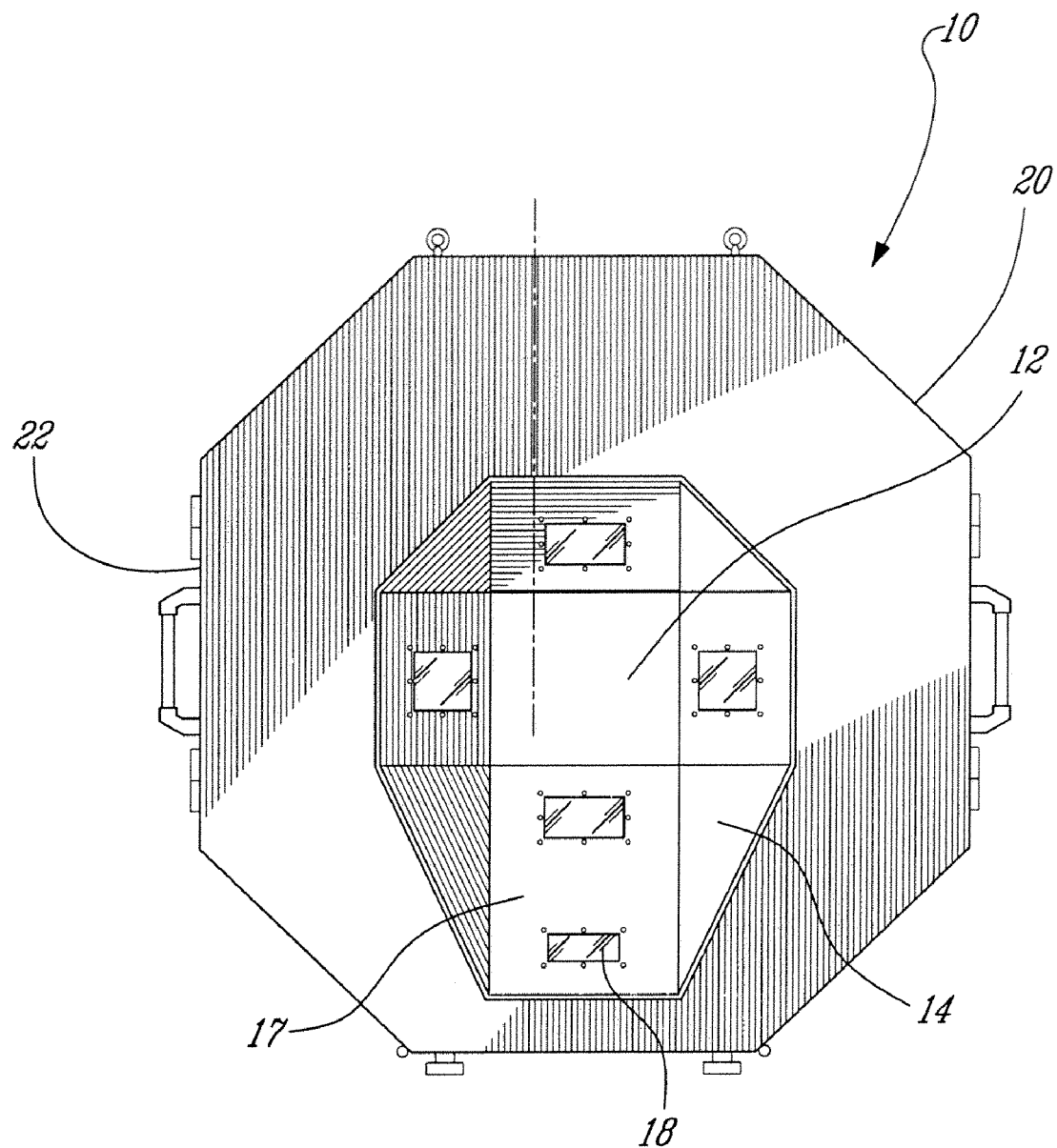
FIG. 2 is a front view of the enclosure of FIG. 1.
Figure 3:
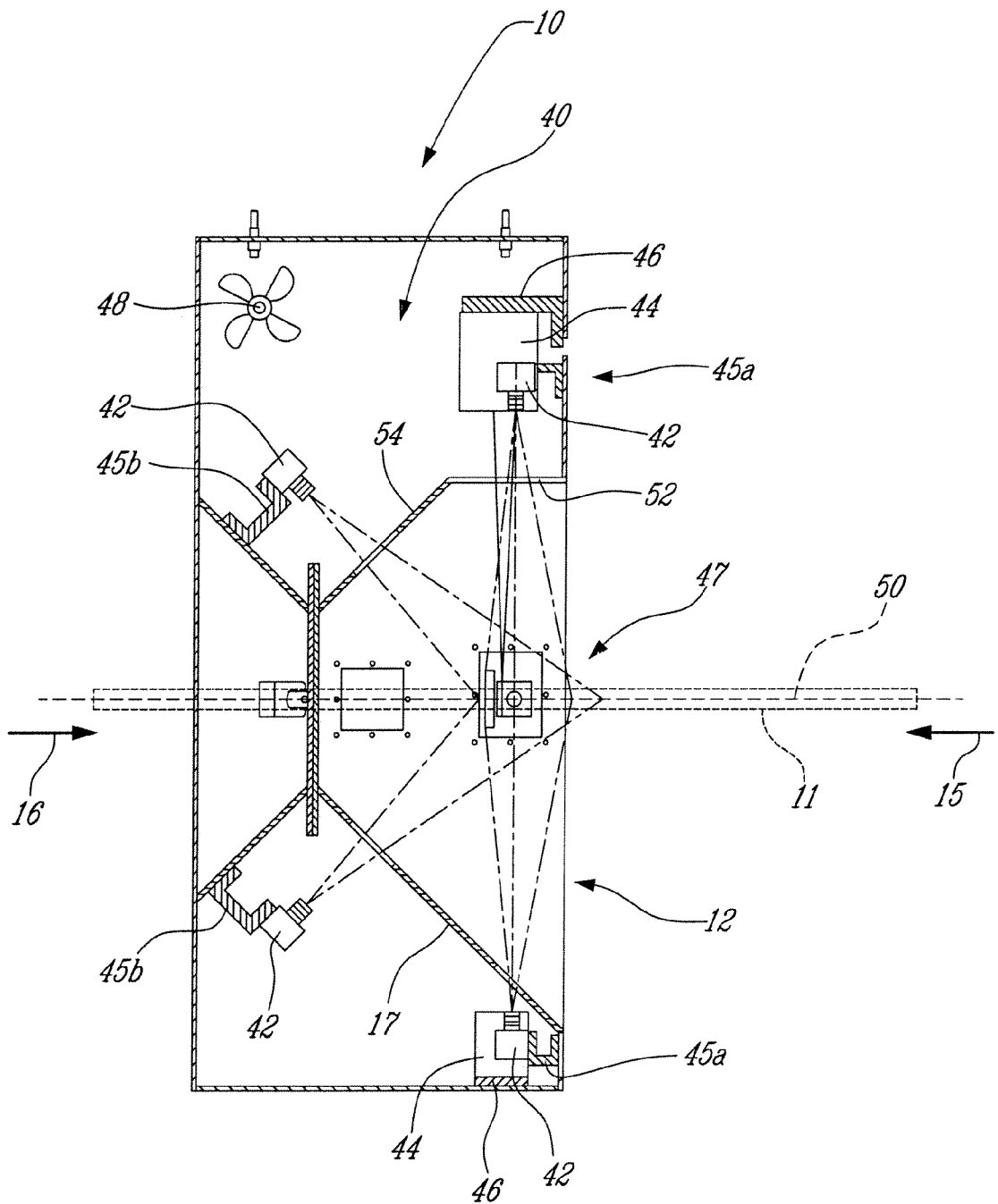
FIG. 3 is a cross-sectional side view of the enclosure of FIG. 1.

Presented in FIG. 2 and concurrently presented in FIG. 3, a bottom portion 17 is positioned in the lower part of the central portion 14 and is therefore operative to downwardly direct debris from the product 11. In accordance with an embodiment of this invention, the bottom portion 17 is a rectangular surface that is inclined downwardly towards the output side 15 of the aperture 12. In FIG. 3, a cross section view of the enclosure 10 is presented with a bottom portion 17 that is shaped as an inverted V, formed by two downwardly opposed inclined surfaces. Such a design allows to downwardly direct debris by gravity from the product towards the output side 15 and the receiving side 16. For such a design to function effectively, the angle of inclination of the bottom portion 17 must be steep enough to allow dust and debris to slide down by force of gravity.

Returning to FIG. 2, the central portion 14 comprises a plurality of translucent windows 18. Alternatively, some or all of these translucent windows could be joined such as to form one or a few large translucent windows 18 or a single large translucent window 18 corresponding to the central portion 14. The translucent windows 18 are typically made of impact resistant glass or translucent plastic.

Moreover, the enclosure 10 comprises a peripheral portion 20 as presented in FIG. 2 and concurrently presented in FIG. 1. The peripheral portion 20 can be made of any impact resistant material. Additionally, the peripheral portion 20 connects to the central portion 14 and provides an enclosed space surrounding the central portion. Just like the central portion 14, the peripheral portion 20 can have many shapes: it can have curved surfaces or flat surfaces or a combination of both. According to an embodiment of this invention, the peripheral portion 20 is an octagonal shaped prism.

As further presented in FIG. 2 and concurrently presented in FIG. 1, the peripheral portion 20 comprises access doors 22 to access an interior of the enclosure 10 for maintenance. The access doors 22 can be placed at any suitable position on the peripheral portion 20. According to an embodiment of this invention, the access doors 22 are placed on each lateral sides of the peripheral portion 20. If preferred, an enclosure 10 design with access doors 22 placed on the central portion 14 or on both central 14 and peripheral 20 portions can be possible.

Referring now to FIG. 3, the enclosure 10 mainly comprises mounting stations 40 that are either independent of the enclosure 10 or are attached to a surface of the enclosure. In the case where the mounting stations 40 are attached to a surface of the enclosure, the mounting stations 40 may be attached either to an inside wall of the peripheral portion 20 or to a wall of the central portion 14. The mounting stations 40 are adapted to mount a single or a plurality of cameras 42 and a single or a plurality of lasers 44. The mounting stations 40 are, furthermore, positioned so that the cameras 42 and lasers 44 are oriented towards an inspection zone 47 within the central portion 14, to scan a surface of the product 11. Moreover, the mounting stations 40 are further positioned so that the cameras 42 and lasers 44 are oriented towards a translucent window 18.

For example, each mounting station 40 may be a single attachment connecting either two cameras and a laser or two lasers and a camera. Alternatively, each mounting station 40 may be made of two or three separate attachments for holding each of these elements. Again, the mounting station 40 could simply be holes in the walls of either the central portion 14 or the peripheral portion 20, given a proper alignment.

In use, each laser 44 on a mounting station 40 projects a non-permanent laser indicator on a surface of the product 11. Both cameras 42 on the same mounting station 40 read the laser indicator. Each set of cameras 42 or each mounting station 40 sends their readings to a central computer for analysis.

According to an embodiment of this invention, each mounting station 40 comprises a first camera attachment 45a, a second camera attachment 45b and a laser attachment 46. The first camera attachment 45a and the second camera attachment 45b are oriented at different angles. In this embodiment, four similar mounting stations 40 are placed in the enclosure 10 to take readings of the product 11 from all four sides.

Figure 4:
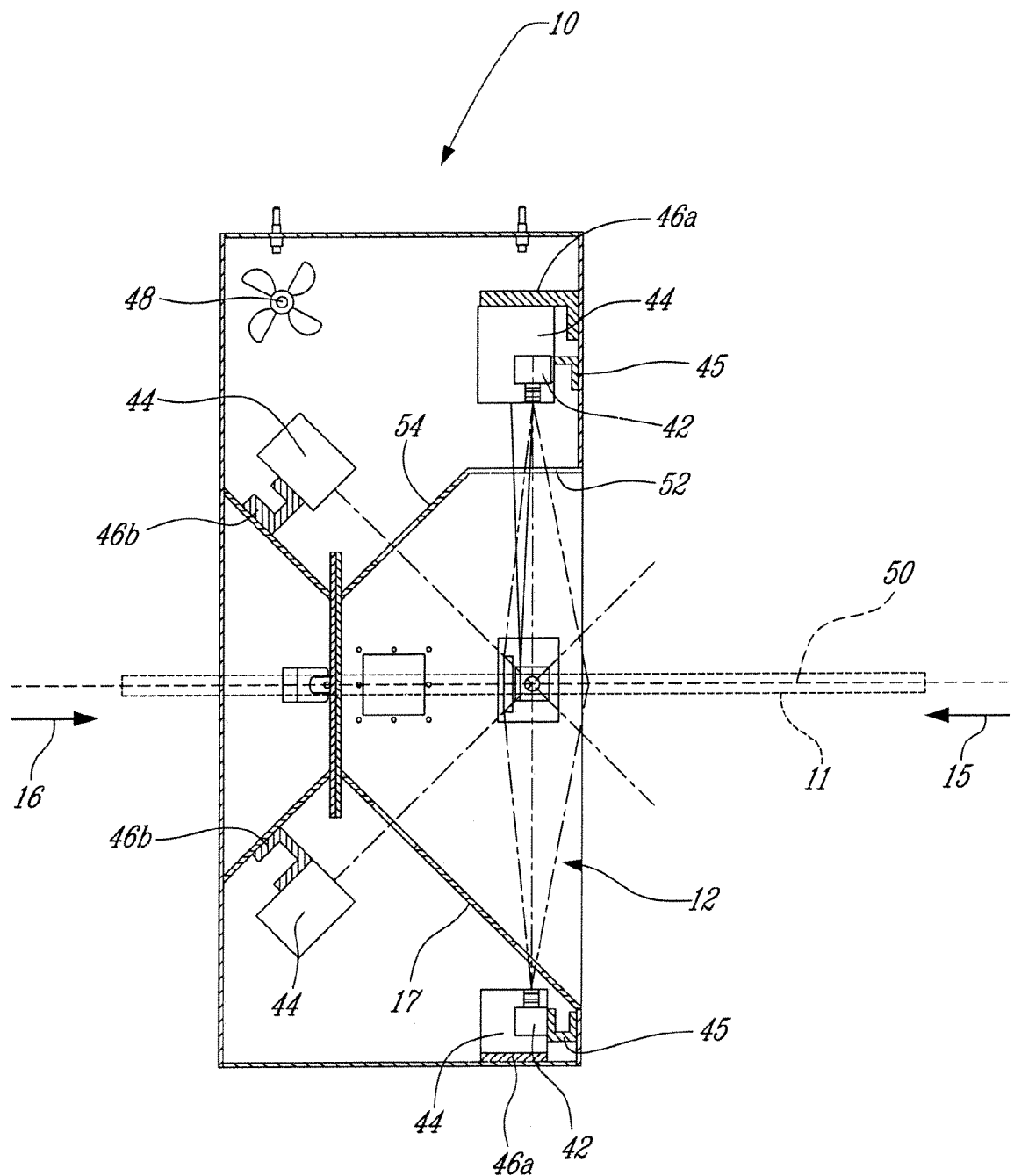
FIG. 4 is another cross-sectional side view of the enclosure of FIG. 1.

Alternatively, as presented in FIG. 4, each mounting station 40 could comprise two lasers 44 and one camera 42. Each mounting station 40 comprises a first laser attachment 46a, a second laser attachment 46b and a camera attachment 45. The first laser attachment 46a and the second laser attachment 46b are oriented at different angles. In this embodiment, four similar mounting stations 40 are placed in the enclosure 10 to take readings of the product 11 from all four sides.

Further presented in FIG. 4 and concurrently presented in FIG. 3, is a temperature control system 48 that can be any temperature control system 48 that is effective enough to keep the temperature inside the enclosure 10 at an operable temperature for the cameras 42 and lasers 44. The temperature control system 48 can be a fan placed in the enclosure 10 with a single or a plurality of openings to allow hot air generated by the cameras 42 and lasers 44 to be released outside the enclosure 10. According to an embodiment of this invention, the temperature control system 48 can further be only the opening without the fan. It may also be acceptable in some applications not to include a temperature control system 48, in cases where the cameras 42 or laser 44 release little heat.

As best seen in FIG. 4 and concurrently in FIG. 3, the product 11 can pass through the enclosure 10 along a longitudinal axis 50. Although in an embodiment of this invention, the longitudinal axis 50 passes through the center of the aperture 12, the longitudinal axis 50 can however be off-center. The inspection zone 47 that is aligned with the longitudinal axis 50 can therefore either be centered or off-centered as long as the passage of the product through the enclosure 10 is not obstructed by the central portion 14.

Figure 5:
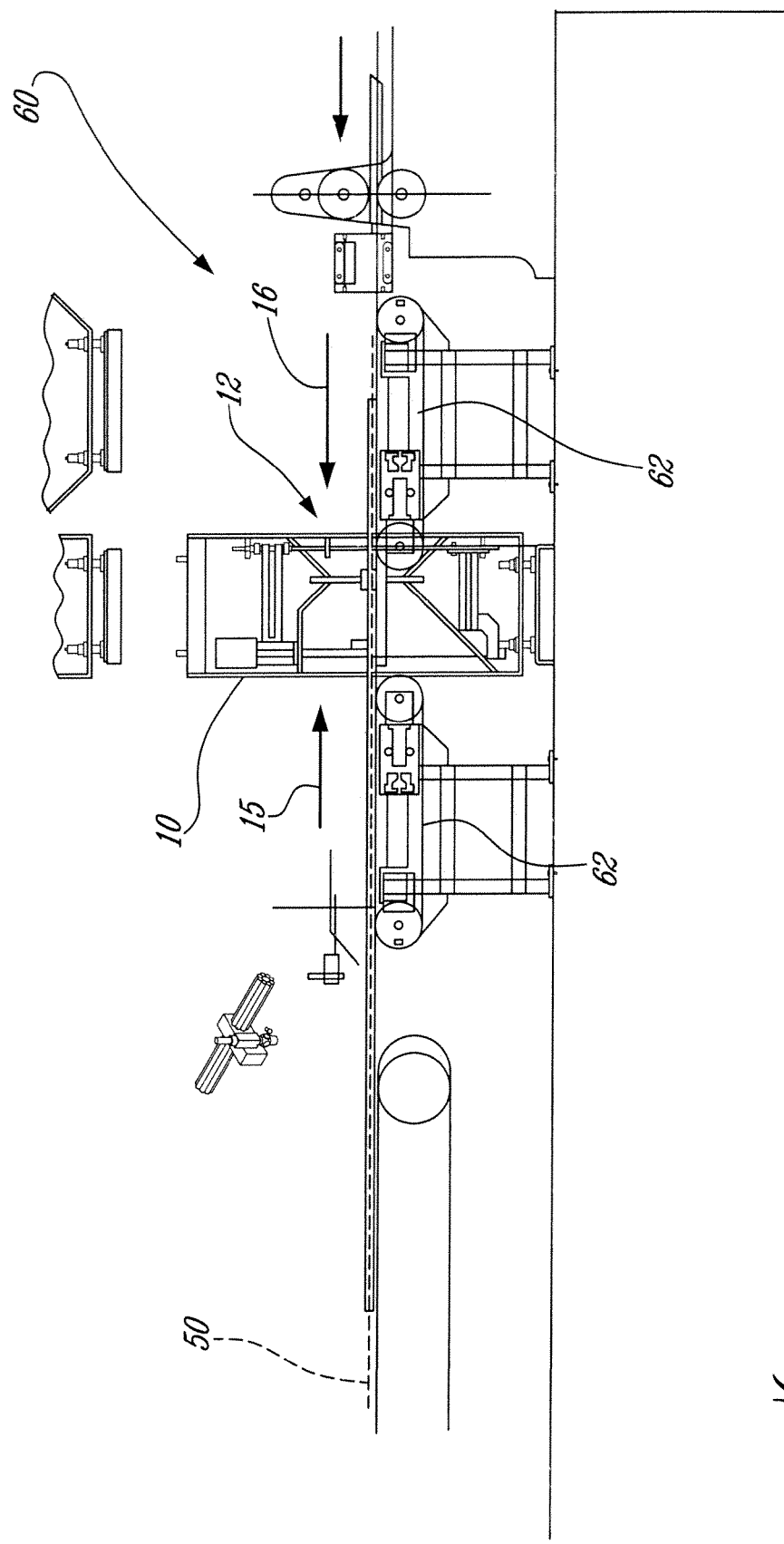
FIG. 5 is a cross-sectional side view of the enclosure of FIG. 1 shown installed on a lumber production line.

Presented in FIG. 5, the enclosure 10 is integrated to a production line 60 and is positioned in order to allow the passage of products 11 through the aperture 12 of the enclosure 10 along the longitudinal axis 50. Conveyors 62 are placed on the receiving side 16 and output side 15 of the enclosure 10 to conduct the products 11 through the aperture 12 of the enclosure 10 along the longitudinal axis 50. Alternatively, there may be only one conveyor 62 placed on either the receiving side 16 or the output side 15 to accommodate tight space in the production line 60.

It will of course be appreciated that many modifications and alternative embodiments are possible within the broad scope of the present invention. For example, in some applications it may be required to have multiple enclosures 10 integrated sequentially to a production line 60, allowing the collection of multiple measurements.

The present invention has been described with regard to preferred embodiments. The description as much as the drawings were intended to help the understanding of the invention, rather than to limit its scope. It will be apparent to one skilled in the art that various modifications may be made to the invention without departing from the scope of the invention as described herein, and such modifications are intended to be covered by the present description.

We claim:

1. An enclosure for a linear inspection system using a plurality of cameras and lasers for the inspection of products, said enclosure comprising:
    a body having:
        a central portion defining an aperture through said body, said central portion being adapted to receive the products through said aperture along a longitudinal axis of said aperture, said central portion having at least one translucent surface;
        a peripheral portion connected to said central portion, said peripheral portion containing a plurality of mounting stations adapted to mount the plurality of cameras and lasers, said plurality of mounting stations being oriented at a mounting angle from each other, said plurality of mounting stations being positioned so that the plurality of cameras and lasers are oriented towards an inspection zone within said central portion, through said at least one translucent surface, said mounting angle being in a plane normal to said longitudinal axis; and
        a bottom portion starting at the central portion and extending over at least a corresponding part of the peripheral portion, the bottom portion directing downwardly debris from the product under inspection in the aperture of the central portion thereby protecting the cameras and lasers mounted in the peripheral portion.

2. The enclosure of claim 1 wherein said translucent surface is a plurality of windows, each one of said plurality of windows being aligned with one of said plurality of mounting stations so as to allow a laser light from each of the plurality of lasers to reach the product oriented along said longitudinal axis, said plurality of windows being further oriented to allow the plurality of cameras to read the laser light on the product.

3. The enclosure of claim 2 wherein each of said plurality of mounting stations comprises one laser attachment adapted to mount one of the plurality of lasers and a first and a second camera attachments, said first and said second camera attachments being adapted to respectively mount a first and a second one of the plurality of cameras.

4. The enclosure of claim 3 comprising four mounting stations.

5. The enclosure of claim 4 wherein said bottom portion has the shape of an inverted V.

6. The enclosure of claim 5 wherein said bottom portion has two of said plurality of windows, one of said two windows being aligned with one of said first camera attachment and another one of said two windows being aligned with one of said second camera attachment.

7. The enclosure of claim 6 wherein said body further comprises access doors to access an interior of said body.

8. The enclosure of claim 7 further comprising a temperature control system to regulate a temperature inside said body.

9. An enclosure for a linear inspection system using at least one camera and at least one laser, said enclosure comprising:
    a central portion defining an aperture adapted to receive products to be inspected, said central portion having at least one translucent surface and defining an inspection zone;
    a peripheral portion connected to said central portion, said peripheral portion being adapted to receive the at least one camera and at least one laser, wherein said enclosure is adapted to orient the at least one camera and at least one laser towards said inspection zone through said at least one translucent surface; and
    a bottom portion starting at the central portion and extending over at least a corresponding part of the peripheral portion, the bottom portion directing downwardly debris from the product under inspection in the aperture of the central portion thereby protecting the cameras and lasers mounted in the peripheral portion.

* * * * *